United States Patent
Vollhardt

(12) 
(10) Patent No.: US 6,274,124 B1
(45) Date of Patent: Aug. 14, 2001

(54) ADDITIVE FOR IMPROVING THE WATER RESISTANCE OF COSMETIC OR DERMATOLOGICAL FORMULATIONS

(75) Inventor: Jürgen Vollhardt, Lincoln Park, NJ (US)

(73) Assignee: Dragoco Gerberding & Co. AG (DE)

( * ) Notice: Subject to any disclaimer, the term of this patent is extended or adjusted under 35 U.S.C. 154(b) by 0 days.

(21) Appl. No.: 09/378,402

(22) Filed: Aug. 20, 1999

(51) Int. Cl.⁷ .............................. A61K 7/42; A61K 7/44; A61K 7/00
(52) U.S. Cl. .............. 424/59; 424/60; 424/400; 424/401
(58) Field of Search ................ 424/59, 60, 400, 424/401

(56) References Cited

U.S. PATENT DOCUMENTS 4,254,105 * 3/1981 Fukuda et al. ...................... 424/401
4,960,764 * 10/1990 Figueroa et al. .................... 424/401

\* cited by examiner

*Primary Examiner*—Shelley A. Dodson
(74) *Attorney, Agent, or Firm*—Pendorf & Cutliff

(57) ABSTRACT

A method for imparting water resistance to or improving water resistance of a cosmetic or dermatological formulation, comprising adding an water resistance enhancing effective amount of 1,2-pentanediol to the otherwise conventional cosmetic or dermatological formulation comprising at least one cosmetic and/or dermatological active agent in a cosmetically and/or pharmaceutically acceptable carrier for topical application to the skin of humans.

22 Claims, No Drawings

ADDITIVE FOR IMPROVING THE WATER RESISTANCE OF COSMETIC OR DERMATOLOGICAL FORMULATIONS

BACKGROUND OF THE INVENTION

Field of the Invention

The present invention relates to cosmetic or dermatological formulations, in particular UV radiation protection formulations.

The skin is an important, but at the same time sensitive, human organ, the care of which is essential for physical and psychological well-being. A large number of skin care compositions have been developed, which are supplied as creams, lotions, oils or gels and contain special skin care active ingredients.

Cosmetic and dermatological skin care compositions are primarily used in order to intensify or restore the natural function of skin as a barrier against environmental influences (for example dirt, chemicals, microorganisms) and against the loss of endogenous substances (for example water, natural fats, electrolytes).

If this function is impaired, increased absorption of toxic or allergenic substances or attack by microorganisms and, as a consequence, toxic or allergic skin reactions may occur.

The aim of cosmetic skin care is furthermore to compensate the loss of fats and water from the skin caused by daily washing. This is important especially if the natural regeneration capacity is inadequate. Skin care products furthermore should protect against environmental influences, in particular sun and wind, and delay the signs of ageing of the skin.

The damaging effect of the ultraviolet part of solar radiation on the skin is generally known. While rays having a wavelength in the range from 200–280 nm (the so-called UVC range) are completely absorbed by the ozone layer in the earth's atmosphere, rays in the range between 280 nm and 315 nm, the so-called UVB range, cause erythema, simple sunburn or even burns of greater or lesser severity on the skin.

Numerous water-soluble or lipid-soluble organic UV filter substances (chemical sunsreen filter substances) are known for protection against UVB radiation, most of these substances being derivatives of 3-benzylidenecamphor, of 4-aminobenzoic acid, of cinnamic acid, of salicylic acid, of benzophenone and also of 2-phenylbenzimidazole (e.g. 2-phenylbenzimidazole-5-sulfonic acid sodium salt). Other examples of UV filter substances can be found in the literature.

UV filter substances are also important for the wavelength range between about 315 and 400 nm, the so-called UVA range, since such rays can also cause damage. It has thus been proved that UVA radiation leads to damage to the elastic and collagenic fibers of the connective tissue, which makes the skin age prematurely and is to be regarded as a cause of numerous phototoxic and photoallergic reactions. The damaging influence of UVB radiation may be intensified by UVA radiation.

UV radiation can also lead to photochemical reactions, the photochemical reaction products then intervening in skin and cell metabolism.

Such photochemical reaction products are chiefly free radical compounds, for example hydroxyl radicals, hydroperoxy radicals and superoxide ions. Further damage is caused by free radical photo-products which are formed in the skin itself and bear high reactivity. However, even singlet oxygen, an excited state of the oxygen molecule which is not in free radical form, can occur with UV irradiation, as can short-lived epoxides and many others. Singlet oxygen, for example, is distinguished from the triplet oxygen usually present (free radical base state) by an increased reactivity. Nevertheless, excited, reactive (free radical) triplet states of the oxygen molecule also exist.

To prevent these reactions, antioxidants and/or agents which trap the radicals can be incorporated into the cosmetic or dermatological formulations, typically in addition to organic UV filter substances.

Furthermore, coated or uncoated inorganic pigments which are known to be used in sunscreen products can help to protect the skin from UV rays. Most inorganic pigments used in cosmetics to protect the skin from UV rays are UV absorbers or UV reflectors. These are oxides of titanium, zinc, iron, zirconium, silicon, manganese, aluminium, cerium and mixtures thereof, as well as modifications. Inorganic pigments are typically used in addition to organic UV filter substances.

Numerous sunscreen compositions (sun protection products) are known for protection against the detrimental effects of exposure to sunlight (UVA and UVB). For various reasons associated especially with being more pleasant to use (gentleness, emollience, ease of application and the like) the sunscreen compositions currently available are typically (but not always) oil-in-water emulsions (namely, a cosmetically acceptable vehicle, carrier or diluent) comprising an aqueous continuous dispersion phase and an oily discontinuous dispersed phase which contain, at various concentrations, one or more organic UV filter substances which are capable of selectively absorbing harmful UV radiation, these filter substances being selected as a function of the degree of desired protection. However, one of the problems presented by this type of sunscreen composition is, in particular, the fact that, once they have been applied to the skin in the form of a film by the users thereof, they have relatively little resistance to water.

Light protection formulations are required and used particularly frequently on bathing beaches and in open-air swimming pools. It is in this case desirable for the light protection formulation to be largely water-resistant, that is to say for it to be washed off from the skin to only a small extent, if at all.

Higher light protection factors, that is to say, for example, those situated above SPF 15, can in general be achieved only by larger amounts of UV filter substances. If a sunscreen product is also still to have a high light protection factor after bathing, the UV filter substance in particular must be retained on the skin.

It is in itself already troublesome if the sunscreen product has to be applied again after bathing. During bathing itself, under certain circumstances the use of a light protection formulation which can be washed off is even irresponsible and harmful to the skin, since water absorbs light in the UVA and UVB range poorly, and consequently represents no noticeable UV protection, not even for submerged areas of skin.

Accordingly, a major object of the present invention is the provision of novel cosmetic or dermatological compositions, in particular sunscreen compositions, which have increased water resistance.

By the term "water resistance" is intended the stability, activity or effect over time of the active ingredient(s) of a given cosmetic or dermatological formulation.

With respect to sunscreen formulations the term "water resistance" is intended the stability over time of the degree of protection in the UVA and/or UVB ranges of sunscreen composition subjected (after application to the skin) to contact with water. The solar protection associated with a given composition is characterized by assigning it a sun protection factor (or SPF) which is mathematically expressed by the ratio of the exposure time necessary to attain the erythematous threshold (minimal erythemal dose) with the UV screen to the time necessary to attain the erythematous threshold without UV screen.

With respect to formulations comprising other (non-UV-protective) cosmetic and/or dermatological agent(s) the term "water resistance" refers to the activity or effect over time of the respective agent(s) of a formulation subjected (after application to the skin) to contact with water.

A further object of the invention is the provision of a method for imparting water resistance to or improving water resistance of a cosmetic or dermatological formulation comprising a cosmetic or dermatological agent in a cosmetically and/or pharmaceutically acceptable carrier (this term comprising all kinds of carriers, vehicles, diluents and the like) for application, in particular topical application, to the skin of humans or animals.

SUMMARY OF THE INVENTION

Surprisingly, it has now been found that by adding an amount of 1,2-pentanediol the water resistance of a (conventional) cosmetic or dermatological formulation comprising at least one cosmetic and/or dermatological active agent in a cosmetically and/or pharmaceutically acceptable carrier for topical application to the skin of humans or animals can be imparted or improved.

The 1,2-pentanediol preferably represents more than 0.5% by weight, relative to the total weight of the resulting water resistant composition, more preferably more than 3% and most preferably from 3 to 6%.

From the European Patent Specification 0 665 904 B1 (Dragoco) it is known that 1,2-pentanediol is suitable as skin-moisture-regulating active ingredient in cosmetic product. However, 1,2-pentanediol is characterized by a virtually unlimited miscibility with water. Thus, it was absolutely unexpected that 1,2-pentanediol can improve the water resistance of a cosmetic or dermatological formulation. It had rather been expected that it would be washed off the skin easily and could therefore have no effect on the water resistance properties of a given formulation. Furthermore, 1,2-propanediol and 1,2-hexanediole do not show a water resistance enhancing effect. As shown below in detail, addition of 1,2 hexanediole rather decreases the water resistance of a cosmetic formulation.

The carrier of the formulations according to the present invention can be in the form of a homogeneous phase formulation or in the form of an emulsion including, but not limited to, oil-in-water, water-in-oil and multiple phase emulsions. These emulsions can cover a broad range of consistencies including thin lotions (which can also be suitable for spray or aerosol delivery), creamy lotions, light creams, heavy creams, and the like. Other suitable topical carriers include anhydrous liquid solvents such as oils and alcohols; aqueous-based single phase liquid solvents (e.g. hydro-alcoholic solvent systems); anhydrous solids and semisolids (such as gels and sticks); and aqueous based gel and mousse systems. Examples of carrier systems useful in the present invention are described in the following four references all of which are incorporated herein by reference in their entirety: "Sun Products Formulary" Cosmetics & Toiletries, vol. 105, pp. 122–139 (December 1990); "Sun Products Formulary", Cosmetics & Toiletries, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

With refererence to sunscreen formulations, the carriers, in total, typically comprise from about 0.1% to about 99.87. by weight of the sunscreen compositions of the present invention (prepared according to the present invention), preferably from about 80% to about 99%, and most preferably from about 85% to about 95%.

A preferred topical carrier of the compositions of the instant invention is an oil-in-water type emulsion. The pH of these oil-in-water emulsion compositions herein is preferably in the range of from about 4.5 to about 9. Additionally, the mean particle size of the dispersed oil phase materials (e.g sunscreen agent, polymer, perfumes, etc.) dispersed in the aqueous phase of these oil-in-water emulsion compositions may be in the range of from about 5 to about 10 microns with greater than about 75% of the particles being less than about 12 microns.

The invention is of particular relevance with respect to sunsreen products, i.e. cosmetic or dermatological formulations which comprise, as a cosmetic or dermatological agent, an organic UV filter substance.

Correspondingly, there is provided a novel method for providing enhanced protection to the skin of humans or animals from the effects of ultraviolet radiation, namely a method comprising topically applying to the skin of the human or animal an effective amount of a sunscreen composition comprising a water resistance improving effective amount of 1,2-pentanediol The organic UV filter substances that can be employed within the concept of the present invention are those typical in the art, in particular those mentioned above.

A formulation suitable for addition of 1,2-pentanediol may, in addition to organic UV filter substances, comprise (a) antioxidants and/or agents which trap radicals or other photochemical reaction products and/or (b) inorganic pigments of the kind mentioned above, i.e. UV absorbers, UV reflectors and the like.

Sunscreen (or antisun) compositions prepared according to the invention, an example is more fully described below, permit retention of sufficient protection factors even in the event of intentional or unintentional wetting of the parts of the body to which they have been applied. This is not only advantageous in economical terms, but further limits or eliminates the risk of accidental "sunburn" for users who forget to reapply the product to the body.

Although the present invention is particularly relevant with respect to sunscreen formulations it is not limited to those formulations. The use of 1,2-pentanediol is likewise effective in connection with cosmetic or dermatological formulations comprising as cosmetic and/or dermatologically active agent(s):

at least one antioxidant like Green Tea catechins, beta Carotene, Polyphenols, Rosemary extract, antioxidative Glycosides, Arbutin, Ascorbic Acid and derivatives thereof, Asiaticoside, Caffeic Acid, Ergothioneine, Ferulic Acid, Glucosylrutin, Hydroquinone, Isoquercitrin, Rosmarinic Acid, Rutin, Tocopherol and Tocopheryl Acetate; and/or at least one anti-inflammatory compound like Bisabolol, Oat Extract, Willowherb extract, Arnica Montana extract, Indomethacin, steroidal anti-inflammatory agents such as hydrocortisone, non-steriodal anti-inflammatory agents (NSAIDs), polyunsaturated fatty acid compounds such as the amides of 5,8,11-eicosatrienoic acid, or glycyrrhetinic acid and mixtures thereof; and/or

- at least one anti-microbial compound like Farnesol, Triclosan, and mixtures thereof; and/or
- at least one antiperspirant like aluminiumchlorhydrate and/or zirconiumchlorhydrate.
- at least one fragrance compound
- at least one skin whitening compound like hydroquinone or rumex extract.

In order to further understand the present invention, the following non-limiting example concerned with sunscreen formulations is provided. All percentages are by weight unless the contrary is stated.

EXAMPLE

Preparation and Comparative Testing of Sunscreen Formulations

In table 1 is given the composition of four different sunscreen O/W formulations. Formulation 2 is a formulation according to the invention, i.e. comprises 1,2-pentanediol. Formulation 1 is a placebo or control sample. And formulations 3 and 4 comprise 1,2 propanediol and 1,2 hexanediol, respectively, i.e. 1,2 alkandiols with a lower or higher number of C atoms than pentanediol.

TABLE 1

Sunscreen formulations

| INCI | 1 Placebo Percentage | 2 1,2-Pentanediol formulation according to the invention Percentage | 3 1,2-Propanediol formulation Percentage | 4 1,2-Hexanediol formulation Percentage | Tradename | Supplier |
|---|---|---|---|---|---|---|
| 1.1 Oil Phase | | | | | | |
| Sodium Dihydroxycetyl Phosphate | 3.0 | 3.0 | 3.0 | 3.0 | Dragophos S [2/918501] | DRAGOCO |
| Bisabolol | 0.1 | 0.1 | 0.1 | 0.1 | Dragosantol [2/012681] | DRAGOCO |
| Octyl Octanoate | 5.0 | 5.0 | 5.0 | 5.0 | Dragoxat EH | DRAGOCO |
| Caprylic/Capric Triglyceride | 10.0 | 10.0 | 10.0 | 10.0 | Neutraloil [2/044115] | DRAGOCO |
| 3-(4 Methylbenzyliden)-Camphor[1] | 4.0 | 4.0 | 4.0 | 4.0 | Eusolex 6300 | Merck |
| Butyl Methoxydibenzoyl-methane[1] | 2.0 | 2.0 | 2.0 | 2.0 | Parsol 1798 | Givauan Roure |
| Octyl-Triazone[1] | 4.0 | 4.0 | 4.0 | 4.0 | Uvinul T150 | BASF |
| Octyl-Methoxycinnamate[1] | 4.0 | 4.0 | 4.0 | 4.0 | Eusolex 2292 | Merck |
| Titanium Dioxide, Alumina, Dimethicon[2] | 2.0 | 2.0 | 2.0 | 2.0 | Eusolex T 2000 | Merck |
| Glyceryl Stearate | 1.5 | 1.5 | 1.5 | 1.5 | Dracorin GMS [2/008484] | DRAGOCO |
| 1.2 Water Phase | | | | | | |
| Aqua | 63.3 | 58.3 | 58.3 | 58.3 | Water | |
| Xanthan Gum | 0.5 | 0.5 | 0.5 | 0.5 | Keltrol | Kelco |
| Pentylene Glycol (1,2-Pentanediol) | 0.0 | 5.0 | 0.0 | 0.0 | Hydrolite 5 [2/016020] | DRAGOCO |
| 1,2-Propanediol | 0.0 | 0.0 | 5.0 | 0.0 | | |
| 1,2-Hexanediol | 0.0 | 0.0 | 0.0 | 5.0 | | |
| Citric Acid | 0.3 | 0.3 | 0.3 | 0.3 | Citric Acid | Merck |
| 1.3 Additional Phase | | | | | | |
| Fragrance | 0.3 | 0.3 | 0.3 | 0.3 | Fragrance | DRAGOCO |
| 1.4 Total | 100.0 | 100.0 | 100.0 | 100.0 | | | remarks:
[1]UV filter substance
[2]inorganic pigments
for sun protection factor and water resistancy cf. table 2–5, respectively Average SPF values determined for the formulations 1–4 are given in the respective tables 2–5. For all four formulations, the addition of the alkanedioles tested had only a neglectable effect on the sun protection factor as such.

For testing the water resistance of a given formulation 1–4 a test method was used which is described in the following references all of which are incorporated herein by reference in their entirety: M. Rohr et al, Parfümerie und Kosmetik 5/98, pages 12–19, Hüthig GmbH, Heidelberg (Germany); Schrader, K, Schrader, A., Die Sonnenschutzfaktorbestimmung: Prüfung der Wasserresistenz, Aktuelle Dermatologie, 20, 4, 1994. For determining the water resistance the SPF was first measured under dry conditions ("without sunscreen formulation" vs "with sunscreen formulation") and then under shower conditions ("without sunscreen formulation" vs "with applied sunscreen formulation after immersion") as desribed in the stated references.

Water resistancies determined for the formulations 1–4 are given in the respective tables 2–5.

As can be derived from tables 2–5 water resistancy was significantly higher for formulation 2 comprising 1,2-pentanediol than for any other tested formulation.

Astonishingly, the water resistancy of the 1,2-hexanediol-formulation was not only lower than that of the 1,2-pentanediol but even lower than the water resistancy of the "placebo"-formulation. Formulation 3 comprising 1,2-propanediole showed a water resistancy similar to those of the placebo.

Thus, in the homologous series 1,2-propanediol, 1,2-pentanediol and 1,2-hexanediol only the 1,2-pentanediol has an water resistance imparting or improving effect.

The preparation of the respective sunscreen formulations 1–4 comprised a four step process: In the first step, an oil phase was composed by mixing the ingredients given in table 1 section 1.1. Care was taken that inorganic pigments like Titanium dioxide, Alumina and Dimethicon were dispersed completely in the oil phase. The dispersion was heated to about 80° C.

In an independent second step, a separate water phase comprising the ingredients according to table 1 section 1.2 was prepared by mixing the indicated components in their respective quantities. The aqueous mixture was also heated to about 80° C.

Both oil and water phase were then combined in a third step of the process. The oil phase was mixed with an Ultra-Turrax stirrer into the water phase for about 5 minutes. The resulting oil in water dispersion was then allowed to cool down to ambient temperature (approx. 18–25° C.) while being gently stirred.

After the temperature of the dispersion had dropped below 40° C., a fragrance mixture (see table 1 section 1.3) was added to complete the sunscreen formulation. The pH of the dispersions was found to be in the range from 6 to 6.5.

For testing the Sun Protection Factor (SPF) of formulations 1–4 the COLIPA method was employed which is described in the follwing references all of which are incorporated herein by reference in their entirety: Dr. Karlheinz Schrader, Skin Care Forum (publisher: Henkel KGaA), No. 10, December 1994, 2–8; M Rohr et al, Parfümerie und Kosmetik 5/98, pages 12–19, Hüthig GmbH, HeidelberG (Germany); COLIPA SPF Test Method, The Recommendation of the COLIPA Task Force "Sun Protection Measurements", October 1994.

TABLE 2

Sun protection factor and water resistancy:
sunscreen formulation comprising Placebo
according to table 1 col. "1"

| character of volunteers | | | | | MED[1] without sunscreen formulation [U/s] | MED[1] with sunscreen formulation [U/s] | SPF[2] | MED[1] after immersion [U/s] | SPF[2] | water resistancy [%] |
|---|---|---|---|---|---|---|---|---|---|---|
| volunteer | age | sex | skin type | ITA | | | | | | |
| 1 | 53 | f | II | 55 | 25 | 650 | 25.0 | 422 | 16.2 | 63.5 |
| 2 | 32 | f | I | 61 | 29 | 650 | 22.4 | 336 | 11.6 | 49.4 |
| 3 | 35 | m | II | 43 | 26 | 650 | 25.0 | 272 | 10.5 | 39.4 |
| 4 | 32 | m | I | 59 | 15 | 300 | 20.0 | 190 | 12.7 | 61.4 |
| 5 | 42 | f | II | 43 | 22 | 550 | 25.0 | 396 | 18.0 | 70.8 |
| 6 | 35 | f | III | 38 | 25 | 625 | 25.0 | 360 | 14.4 | 55.8 |
| average SPF[2] | | | | | | | 24 | | 14 | |
| water resistancy [%] | | | | | | | | | | 56.7 | remarks:
MED[1] minimal erythemal dose
SPF[2] sun protection factor

TABLE 3

Sun protection factor and water resistancy:
sunscreen formulation comprising 1,2-pentanediol
(acc. to the invention) according to table 1 col. "2"

| character of volunteers | | | | | MED[1] without sunscreen formulation [U/s] | MED[1] with sunscreen formulation [U/s] | SPF[2] | MED[1] after immersion [U/s] | SPF[2] | water resistancy [%] |
|---|---|---|---|---|---|---|---|---|---|---|
| volunteer | age | sex | skin type | ITA | | | | | | |
| 1 | 19 | m | II | 54 | 20 | 500 | 25.0 | 400 | 20.0 | 79.2 |
| 2 | 20 | m | II | 49 | 16 | 325 | 20.3 | 208 | 13.0 | 62.1 |
| 3 | 20 | m | I | 62 | 29 | 725 | 25.0 | 583 | 20.1 | 79.6 |
| 4 | 52 | f | III | 41 | 23 | 475 | 20.7 | 304 | 13.2 | 62.2 |
| 5 | 53 | f | I | 63 | 13 | 325 | 25.0 | 205 | 15.8 | 61.5 |
| 6 | 35 | m | III | 32 | 22 | 450 | 20.5 | 350 | 15.9 | 76.6 |

TABLE 3-continued

Sun protection factor and water resistancy:
sunscreen formulation comprising 1,2-pentanediol
(acc. to the invention) according to table 1 col. "2"

| | | | character of volunteers | | | | | | | |
|---|---|---|---|---|---|---|---|---|---|---|
| volunteer | age | sex | skin type | ITA | MED[1] without sunscreen formulation [U/s] | MED[1] with sunscreen formulation [U/s] | SPF[2] | MED[1] after immersion [U/s] | SPF[2] | water resistancy [%] |
| average SPF[2] | | | | | | | 23 | | 16 | |
| water resistancy [%] | | | | | | | | | | 70.2 | remarks:
MED[1] minimal erythemal dose
SPF[2] sun protection factor

TABLE 4

Sun protection factor and water resistancy:
sunscreen formulation comprising 1,2-propanediol
according to table 1 col. "3"

| | | | character of volunteers | | | | | | | |
|---|---|---|---|---|---|---|---|---|---|---|
| volunteer | age | sex | skin type | ITA | MED[1] without sunscreen formulation [U/s] | MED[1] with sunscreen formulation [U/s] | SPF[2] | MED[1] after immersion [U/s] | SPF[2] | water resistancy [%] |
| 1 | 25 | m | II | 45 | 30 | 600 | 20.0 | 390 | 13.0 | 63.2 |
| 2 | 24 | m | II | 48 | 37 | 740 | 20.0 | 373 | 10.1 | 47.8 |
| 3 | 58 | f | II | 47 | 27 | 660 | 24.4 | 429 | 15.9 | 63.5 |
| 4 | 38 | f | I | 64 | 37 | 740 | 20.0 | 481 | 13.0 | 63.2 |
| 5 | 42 | m | III | 41 | 20 | 480 | 24.0 | 312 | 15.6 | 63.5 |
| average SPF[2] | | | | | | | 22 | | 14 | |
| water resistancy [%] | | | | | | | | | | 60.2 | remarks:
MED[1] minimal erythemal dose
SPF[2] sun protection factor

TABLE 5

Sun protection factor and water resistancy:
sunscreen formulation comprising 1,2-hexanediol
according to table 1 col. "4"

| | | | character of volunteers | | | | | | | |
|---|---|---|---|---|---|---|---|---|---|---|
| volunteer | age | sex | skin type | ITA | MED[1] without sunscreen formulation [U/s] | MED[1] with sunscreen formulation [U/s] | SPF[2] | MED[1] after immersion [U/s] | SPF[2] | water resistancy [%] |
| 1 | 50 | f | I | 61 | 35 | 380 | 25.3 | 156 | 10.4 | 38.6 |
| 2 | 35 | m | II | 33 | 35 | 700 | 20.0 | 209 | 6.0 | 26.2 |
| 3 | 42 | f | II | 39 | 26 | 420 | 16.2 | 273 | 10.5 | 62.7 |
| 4 | 37 | m | III | 32 | 36 | 580 | 16.1 | 299 | 8.3 | 48.3 |
| 5 | 20 | m | III | 29 | 34 | 680 | 20.0 | 286 | 8.4 | 39.0 |
| 6 | 49 | f | I | 57 | 27 | 660 | 24.4 | 249 | 9.2 | 35.1 |
| average SPF[2] | | | | | | | 20 | | 9 | |
| water resistancy [%] | | | | | | | | | | 41.7 | remarks:
MED[1] minimal erythemal dose
SPF[2] sun protection factor

I claim:

1. A method for imparting water resistance to or improving water resistance of a cosmetic or dermatological formulation comprising at least one cosmetic and/or dermatological active agent in a cosmetically and/or pharmaceutically acceptable carrier for topical application to the skin of humans or animals comprising: adding a water resistance improving effective amount of 1,2-pentanediol to said formulation.

2. The method of claim 1 wherein the cosmetic or dermatological formulation comprises at least one organic UV filter substance, the water resistance of which is improved by the presence of 1,2-pentanediol.

3. The method of claim 2, wherein the organic UV filter substance is selected from the group comprising derivatives of 3-benzylidenecamphor, of 4-aminobenzoic acid, of cinnamic acid, of salicylic acid, of benzophenone and of 2-phenylbenzimidazole.

4. The method of claim 1 wherein the cosmetic or dermatological formulation comprises coated or uncoated inorganic pigments, the water resistance of which is improved by the presence of 1,2-pentanediol.

5. The method of claim 3, wherein the inorganic pigments comprise pigments of a metal oxide.

6. The method of claim 4, wherein the metal oxide pigments are selected from the group comprising metal oxides pigments of titanium, zinc, iron, zirconium, silicon, manganese, aluminium, cerium and mixtures thereof.

7. The method of claim 1 wherein the cosmetic or dermatological formulation comprises at least one antioxidant the water resistance of which is improved by the presence of 1,2-pentanediol.

8. The method of claim 6, wherein the antioxidant is selected from the group comprising Green Tea catechins, beta Carotene, Polyphenols, Rosemary extract, antioxidative Glycosides, Arbutin, Ascorbic Acid and derivatives thereof, Asiaticoside, Caffeic Acid, Ergothioneine, Ferulic Acid, Glucosylrutin, Hydroquinone, Isoquercitrin, Rosmarinic Acid, Rutin, Tocopherol and Tocopheryl Acetate, and mixtures thereof.

9. The method of claim 1, wherein the cosmetic or dermatological formulation comprises at least one anti-inflammatory compound the water resistance of which is improved by the presence of 1,2-pentanediol.

10. The method of claim 8, wherein the anti-inflammatory compound is selected from the group comprising Bisabolol, Oat Extract, Willowherb extract, Arnica Montana extract, Indomethacin, steroidal anti-inflammatory agents such as hydrocortisone, non-steriodal anti-inflammatory agents (NSAIDs), polyunsaturated fatty acid compounds such as the amides of 5,8,11-eicosatrienoic acid, or glycyrrhetinic acid and mixtures thereof.

11. The method of claim 1, wherein the cosmetic or dermatological formulation comprises at least one anti-microbial compound the water resistance of which is improved by the presence of 1,2-pentanediol.

12. The method of claim 10, wherein the anti-microbial compound is selected from the group comprising Farnesol and Triclosan, and mixtures thereof.

13. The method of claim 1, wherein the cosmetic or dermatological formulation comprises at least one antiperspirant the water resistance of which is improved by the presence of 1,2-pentanediol.

14. The method of claim 12, wherein the antiperspirant is selected from the group comprising aluminiumchlorhydrate, zirconiumchlorhydrate.

15. The method of claim 1, wherein the cosmetic or dermatological formulation comprises at least one fragrance compound.

16. The method of claim 1, wherein the cosmetic or dermatological formulation comprises at least one skin whitening compound.

17. The method of claim 15, wherein the skin whitening compound is selected from the group comprising hydroquinone and rumex extract.

18. The method of claim 1, wherein 1,2-pentanediol is added in an amount of more than 0.5 percent by weight, based on the weight of the resulting formulation.

19. The method of claim 1, wherein 1,2-pentanediol is added in an amount of more than 3 percent by weight, based on the weight of the resulting formulation.

20. The method of claim 1, wherein 1,2-pentanediol is added in an amount in the range from 3 to 6 percent by weight, based on the weight of the resulting formulation.

21. A method for providing enhanced protection to the skin of humans or animals from the effects of ultraviolet radiation, said method comprising topically applying to the skin of the human or animal an effective amount of a sunscreen composition comprising a water resistance improving effective amount of 1,2-pentanediol.

22. A method for increasing water resistance and skin residency time of a cosmetic or dermatological formulation comprising at least one cosmetic and/or dermatological active agent in a cosmetically and/or pharmaceutically acceptable carrier for topical application to the skin of humans or animals comprising: adding to said cosmetic or dermatological formulation a water resistance improving effective amount of 1,2-pentanediol to said.

* * * * *